United States Patent
Ping et al.

(10) Patent No.: US 12,180,345 B2
(45) Date of Patent: Dec. 31, 2024

(54) METHOD FOR IMPROVING TRIBOELECTRIC OUTPUT PERFORMANCE OF PROTEIN FILM BY CHANGING PROTEIN STRUCTURE

(71) Applicant: ZHEJIANG UNIVERSITY, Zhejiang (CN)

(72) Inventors: Jianfeng Ping, Zhejiang (CN); Chengmei Jiang, Zhejiang (CN); Yibin Ying, Zhejiang (CN)

(73) Assignee: ZHEJIANG UNIVERSITY, Zhejiang (CN)

( * ) Notice: Subject to any disclaimer, the term of this patent is extended or adjusted under 35 U.S.C. 154(b) by 247 days.

(21) Appl. No.: 17/775,894

(22) PCT Filed: Oct. 29, 2020

(86) PCT No.: PCT/CN2020/124871
§ 371 (c)(1),
(2) Date: May 11, 2022

(87) PCT Pub. No.: WO2022/041465
PCT Pub. Date: Mar. 3, 2022

(65) Prior Publication Data
US 2022/0380559 A1    Dec. 1, 2022

(30) Foreign Application Priority Data
Aug. 25, 2020 (CN) .......................... 202010863403.4

(51) Int. Cl.
*C08J 5/18* (2006.01)
*C07K 1/02* (2006.01)
(Continued)

(52) U.S. Cl.
CPC .................... *C08J 5/18* (2013.01); *C07K 1/02* (2013.01); *C07K 14/415* (2013.01); *H02N 1/04* (2013.01); *C08J 2389/00* (2013.01)

(58) Field of Classification Search
CPC .......... C08J 5/18; C08J 2389/00; C07K 1/02; C07K 14/415; H02N 1/04
See application file for complete search history.

(56) References Cited

U.S. PATENT DOCUMENTS

2018/0346690 A1    12/2018    Wu et al.

FOREIGN PATENT DOCUMENTS

| CN | 110311586 | 10/2019 |
|---|---|---|
| CN | 110387056 | 10/2019 |

OTHER PUBLICATIONS de Souza et al. "Characterization of rice starch and protein obtained by a fast alkaline extraction method" Food Chemistry 191 (2016) 36-44 (Year: 2016).*

(Continued)

*Primary Examiner* — Robert S Walters, Jr.
(74) *Attorney, Agent, or Firm* — JCIPRNET

(57) ABSTRACT

The invention discloses a method for improving triboelectric output performance of a protein film by changing a protein structure. Indissolvable protein powder and a trace amount of another protein powder are co-dissolved in a strong alkaline aqueous solution and maintained for a period of time, and then acidifying treatment is performed to achieve neutral condition to allow charge redistribution to induce refolding of the protein, which results in burying of hydrophobic groups of the protein and exposure of charged groups. Therefore, the solubility of the protein is remarkably improved, and a uniform protein solution is formed under a neutral condition. The plant protein structure is changed through a pH cycle process, a surface group exposure (Continued)

condition is adjusted, and the output performance of the plant protein film is greatly improved.

8 Claims, 2 Drawing Sheets

(51) Int. Cl.
*C07K 14/415* (2006.01)
*H02N 1/04* (2006.01)

(56) References Cited

OTHER PUBLICATIONS

English machine translation of Ping et al. (CN110311586).*
"International Search Report (Form PCT/ISA/210) of PCT/CN2020/124871", mailed on May 25, 2021, pp. 1-5.
"Written Opinion of the International Searching Authority (Form PCT/ISA/237) of PCT/ CN2020/124871", mailed on May 25, 2021, pp. 1-4.
Office Action of China Counterpart Application, with English translation thereof, issued on Mar. 24, 2021, pp. 1-4.
Robert Ccorahua et al., "Enhanced-performance bio-triboelectric nanogenerator based on starch polymer electrolyte obtained by a cleanroom-free processing method", Nano Energy, vol. 59, Mar. 2019, pp. 610-618.
Yaojie Han et al., "Fish Gelatin Based Triboelectric Nanogenerator for Harvesting Biomechanical Energy and Self-Powered Sensing of Human Physiological Signals", ACS Appl. Mater. Interfaces, vol. 20, Mar. 2020, pp. 16442-16450.
Kaushik Parida et al., "Progress on triboelectric nanogenerator with stretchability, self-healability and bio-compatibility", Nano Energy, vol. 59, Jan. 2019, pp. 237-257.

* cited by examiner

METHOD FOR IMPROVING TRIBOELECTRIC OUTPUT PERFORMANCE OF PROTEIN FILM BY CHANGING PROTEIN STRUCTURE

CROSS-REFERENCE TO RELATED APPLICATION

This application is a 371 of international application of PCT application serial no. PCT/CN2020/124871, filed on Oct. 29, 2020, which claims the priority benefit of China application no. 202010863403.4, filed on Aug. 25, 2020. The entirety of each of the above-mentioned patent applications is hereby incorporated by reference herein and made a part of this specification.

FIELD OF THE DISCLOSURE

The disclosure relates to a method for improving the triboelectric output performance of a protein film, in particular to a method for improving the triboelectric output performance of a protein film by modifying the protein structure, improving the performance thereof as an electron-donating layer of a triboelectric nanogenerator, and greatly improving the outputs of the triboelectric nanogenerator.

DESCRIPTION OF RELATED ART

With the growing demand for clean and sustainable energy, various technologies such as photovoltaics, piezoelectrics, thermoelectrics, osmotic power generation, etc. are rapidly developed to convert various forms of renewable energy, such as mechanical, chemical, solar energy, thermal energy and wind energy in the surrounding environment into electricity. However, it is commonly known that mechanical energy is one of the most abundant and ubiquitous energy sources available in daily life. Triboelectric nanogenerators have developed rapidly in recent years as a new technology suitable for converting surrounding mechanical energy into electrical energy at any time and any place. However, such technology has also led to the increase of e-waste and inevitably caused a burden on the environment. Moreover, due to the development of wearable electronic devices as well as implantable medical devices, eco-friendly biological triboelectric nanogenerators have attracted extensive attention, and thus sustainable biomaterials have been widely developed. To date, various biomaterials such as fibroin, starch, cellulose, chitosan, gelatin, and bacterial nanocellulose have been adopted as dielectric layer materials for triboelectric nanogenerators to replace synthetic polymers and other non-biocompatible materials. However, the cumbersome processing steps make it difficult to use the above materials in practical applications.

As a typical by-product of the starch industry, plant protein is derived from abundant sources, but it is difficult to apply vegetable protein in the food field due to a strict extraction condition and the allergenic issue. As a result, plant protein is usually used as boiler fuel and animal feed, or even discarded, causing a huge waste of resources. Moreover, considering the abundant amide groups (an electron donor group) on the protein backbone and diversity of protein structures, thereof, plant protein may be an outstanding candidate for the design of novel triboelectric nanogenerators.

In recent years, extensive research has been conducted on the protein structure modification technology. The technology may transform indissolvable plant proteins from an aggregated state to a highly hydrophilic structure. That is, a type of protein and a trace amount of another protein are co-dissolved in a strong alkaline solution and maintained for a short period of time under the condition, then an acidifying treatment is performed to achieve neutral condition to allow charge redistribution to induce refolding of the protein. This process, known as pH-cycle, will dramatically alter the original protein properties, allowing the protein to exhibit extraordinary properties, including enhanced solubility, emulsifying and film-forming properties, and changes in mesostructure.

SUMMARY OF THE DISCLOSURE

In order to solve the existing problems in the technology of biological triboelectric nanogenerator, the purpose of the present disclosure is to provide a method for improving the triboelectric output performance of a protein film by modifying the protein structure. For the first time, the mechanism of triboelectric charging behaviour related to protein structure has been studied, so as to improve the output performance of plant protein as a triboelectric material.

The technical scheme adopted in the present disclosure is:

The method of the disclosure includes pretreating a protein powder to obtain a protein solution, which is used as a film-forming solution. Then a plasticizer is added, and a heat treatment is performed to denature the protein to obtain a more extensive structure required for film-forming. Finally, the solvent is evaporated and dried to obtain a protein film with a uniform texture, good transparency and flexibility. The obtained protein film is characterized in the following:

The protein powder is pretreated to obtain a protein solution. Specifically, indissolvable protein powder and a trace amount of another protein powder are co-dissolved in a strong alkaline aqueous solution and maintained for a period of time, and then an acidifying treatment is performed to achieve neutral condition to allow charge redistribution to induce refolding of the protein, which results in burying of hydrophobic groups of the protein and exposure of charged groups. In this manner, the solubility of the protein is remarkably improved, and a uniform protein solution is formed under a neutral condition.

Said another protein powder is specifically a protein powder with a protein structure different from the indissolvable protein powder, and a mass ratio between the indissolvable protein powder and said another protein powder is 1:0.005 to 1:0.1.

The strong alkaline aqueous solution is a sodium hydroxide solution to adjust pH to a range between 11 and 13, and is maintained for a period of time for 2 to 8 hours.

The acidifying treatment adopts the step of adding hydrochloric acid and adjusting pH to a range between 6 and 8.

The plasticizer is polyol, and the amount of addition of the plasticizer is 20 to 50% (w/w) of the protein.

The process of obtaining the protein solution from the pretreatment is carried out under a stirring condition.

The protein film serves as the electron-donating layer of the triboelectric nanogenerator, which is stacked face-to-face with a triboelectric negative layer. The respective rear surfaces of the protein film and the triboelectric negative layer are adhered or plated with electrodes, or only the rear surface of the protein film or the rear surface of the triboelectric negative layer is provided with a grounded electrode, thereby fabricating the triboelectric nanogenerator.

The indissolvable protein powder is a kind of indissolvable plant protein such as rice protein, peanut protein isolate, soybean protein isolate, wheat glutelin, zein and the like.

Said another protein powder includes casein, whey protein, soy protein isolate, wheat glutelin protein, peanut protein isolate and the like.

The triboelectric negative layer may be made of many materials, such as polytetrafluoroethylene (Teflon), polydimethylsiloxane (PDMS), polyvinyl chloride (PVC), polyimide (Kapton), silicon rubber (Ecoflex), polylactic acid (PLA), etc., all of which may be used as materials for triboelectric nanogenerators.

The triboelectric nanogenerator has four operating modes, including a vertical contact-separation mode, a lateral-sliding mode, a single-electrode mode and a freestanding triboelectric-layer mode. Taking the single-electrode mode as an example, the protein film and triboelectric negative layer are combined together, and electrode is placed at the bottom and grounded, thus forming a triboelectric nanogenerator. When the triboelectric negative layer at the top is close to or separated from the protein film at the bottom, the local electric field distribution will change. As a result, electrons will flow back and forth between the electrode and the ground, thus balancing the potential difference on the electrode.

In the present disclosure, the measure of dissolving the protein powder in a strong alkaline aqueous solution or an ethanol aqueous solution in the conventional method is changed into co-dissolving the protein powder and a trace amount of another protein and performing a pretreatment to achieve neutral condition to obtain a protein solution.

The disclosure uses pH-cycle to make the plant protein self-assemble to form a film under a neutral condition, which significantly improves the output performance of the plant protein as an electron-donating layer of a triboelectric nanogenerator, and investigates the mechanism for the performance improvement and its forming mechanism, thereby providing opportunities for the application of insoluble or indissolvable plant protein in implantable and wearable triboelectric nanogenerators.

Compared with the conventional technology, the present disclosure is characterized in the following:

First, due to the complex structure of plant proteins, many electron-donating groups are not fully exposed on the surface, which remarkably limits its tribo-electron-donating properties. The present disclosure changes the structure of plant proteins through the pH-cycle process, thereby adjusting the exposure of groups on the surface. In this manner, more electron-donating groups are exposed, and electron-withdrawing groups such as carboxyl groups are buried, thereby considerably improving the output performance of plant protein films.

Secondly, through the pH-cycle, the plant protein that is originally insoluble in a neutral condition but soluble in the strong alkaline aqueous solution may have remarkably improved solubility, so that protein aqueous solution may be formed under the neutral condition and self-assembled into films. In this way, the alkali residue is avoided, so that plant protein film is able to be applied in the fields of implantable medical devices and wearable electronic devices.

Moreover, compared with other biological materials, the preparation process of plant protein film is simple, the source of plant protein is abundant, and the cost is low because plant protein is often discarded as waste.

Finally, the mechanism and possible forming mechanism of the protein film of experimental group with enhanced triboelectric output performance after subjected to pH-cycle are explored through a series of characterization methods.

DESCRIPTION OF EMBODIMENTS

Figure 1:
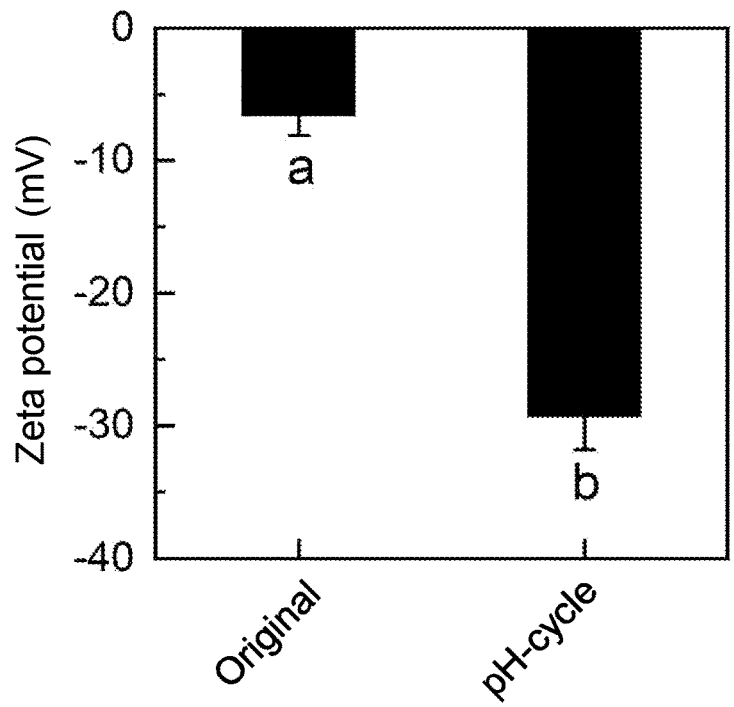
FIG. 1 is a Zeta-potential of a protein solution without undergoing pH-cycle and a protein solution of experimental group undergoing pH-cycle in the present disclosure.

The present disclosure will be further described below in conjunction with the accompanying drawings and specific implementations.

In the specific implementation, the treatments for the control group and the experimental group are carried out as follows:

For preparing a plant protein film of the control group, the plant protein film was prepared through casting. First, a film-forming solution was prepared, an indissolvable protein powder was dissolved in an appropriate solvent: alkaline water or ethanol aqueous solution, and then an appropriate amount of glycerol was added as a plasticizer. After a heat treatment was carried out, the protein was denatured to obtain a more extensive structure required for film forming, and finally the solvent was evaporated to obtain a protein film with uniform texture, a certain level of transparency and good flexibility.

For preparing a plant protein film of the experimental group, the plant protein film was prepared through a deposition method. First, a film-forming solution was prepared; an indissolvable protein powder and a trace amount of another protein were co-dissolved in a strong alkaline aqueous solution (1-5%, w/w), and maintained for a short period of time under the condition. Thereafter, acidifying treatment was performed to achieve neutral condition to allow charge redistribution to induce refolding of the protein, which results in burying of hydrophobic groups of the protein and exposure of charged groups. Therefore, the solubility of the protein is remarkably improved. After the salts and other small molecular compounds in the protein solution were removed by dialysis, a homogeneous protein solution was formed under a neutral condition. After obtaining the protein solution, the same procedure for the control group was carried out: an appropriate amount of glycerol was added as a plasticizer (so as to reduce the interaction between protein chains to improve the tensile properties of the film, enhance flexibility so the film is not easily cracked), and the protein was denatured through a heat treatment to obtain a more extensive structure required for film forming. Finally, the solvent was evaporated to obtain a protein film with uniform texture, a certain level of transparency, and good flexibility.

After the protein films of the control group and the experimental group were equilibrated with humidity, they were used as tribo-electron-donating layers respectively, and their output electrical properties were measured and compared.

A plasticizer (such as glycerol) with a content of 20 to 50% (w/w) relative to the protein by mass was added to the two groups of protein solutions. After heating and stirring in a water bath at 50 to 70° C. for 30 to 60 minutes, and degassing under vacuum for 10 minutes, the solutions were poured into molds and placed in an oven to dry at 40 to 60° C. Finally, the dried films were peeled off, and the moisture was equilibrated under certain temperature and humidity conditions for subsequent tests.

EMBODIMENTS

Embodiment 1

First, a protein solution of the experimental group was prepared. 1.25 g of indissolvable rice glutelin was dispersed in 25 mL of an aqueous solution (5%, w/w), and 0.0125 g of another variety of rice glutelin was added. Then, 1 M of sodium hydroxide was added to adjust the solution to pH 12, so that the protein was fully dissolved in strong alkali. After stirring for 3 hours, 1 M of hydrochloric acid was added to acidify the solution to pH 10.5, and then 0.1 M of hydrochloric acid was used to adjust the solution to pH 7.5. The entire pH-cycle process needs to be carried out under a stirring condition. Finally, the salts and other small molecular compounds in the protein solution were removed by dialysis to obtain the film-forming solution of the experimental group.

As shown in FIG. 1, compared with the negative control group (rice glutelin without undergoing any treatment and fully hydrated in water), the absolute value of the zeta potential of the protein solution of experimental group was higher, indicating that the protein solution of experimental group had a better stability under a neutral condition. The better stability provides prerequisites for forming film from indissolvable rice glutelin through casting under a neutral condition.

Embodiment 2

First, a protein solution of the experimental group was prepared. 1.25 g of indissolvable rice glutelin was dispersed in 25 mL of an aqueous solution (5%, w/w), and 0.0125 g of another variety of rice glutelin was added. Then, 1 M of sodium hydroxide was added to adjust the solution to pH 12, so that the protein was fully dissolved in strong alkali. After stirring for 3 hours, 1 M of hydrochloric acid was added to acidify the solution to pH 10.5, and then 0.1 M of hydrochloric acid was used to adjust the solution to pH 7.5. The entire pH-cycle process needs to be carried out under a stirring condition. Finally, the salts and other small molecular compounds in the protein solution were removed by dialysis to obtain the film-forming solution of the experimental group.

Secondly, a protein solution of the control group was prepared. 1.25 g of indissolvable rice glutelin was dispersed in 25 mL of an aqueous solution (5%, w/w). Then, 1 M of sodium hydroxide was added to adjust the solution to pH 12, so that the protein was fully dissolved in strong alkali. After stirring for 3 hours, the film-forming solution of the control group was obtained.

Then, 0.375 g of glycerol was added to the protein solutions of the two groups respectively, and heated and stirred at 60° C. for 30 minutes, and degassed under vacuum for 10 minutes to remove air bubbles. Finally, the final film-forming solution was poured into a circular Teflon mold (3 cm in diameter) and dried in an oven at 40° C. Finally, the dried film was peeled off and placed in a constant temperature and humidity incubator at 25° C. and 40% relative humidity for 24 hours as a tribo-electron-donating layer for testing.

Preparation of triboelectric negative layer: a polydimethylsiloxane (PDMS) elastomer and a curing agent were mixed with a mass ratio of 10:1 and stirred evenly, and the mixture was poured into a Teflon mold and cured in an oven at 90° C. for 2 hours to obtain a PDMS film. Finally, the film was cut into a rectangle with a size of 1.5 cm×1.5 cm as a triboelectric negative layer for testing.

Figure 2:
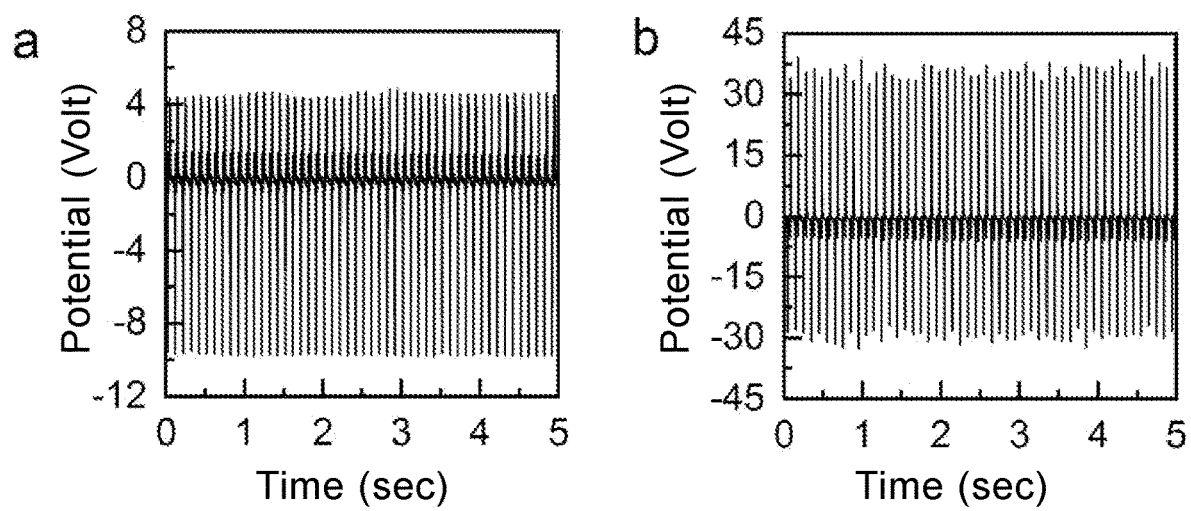
FIG. 2 is a graph showing the triboelectric output voltage of (a) a protein film of the control group (pH 12) and (b) a protein film of experimental group undergoing pH-cycle in the present disclosure.

Preparation of triboelectric nanogenerator: The above rice glutelin film and PDMS film were combined to form a triboelectric pair, and an aluminum foil was placed on one side of the protein film as an electrode to form a triboelectric nanogenerator, and the voltage signal thereof was measured with an oscilloscope. As shown in FIG. 2, the output voltage of the protein film of experimental group was nearly 4 times higher than the protein film of the control group, indicating that after the pH-cycle process, the triboelectric output electrical performance of the protein film was remarkably improved.

Embodiment 3

1.25 g of indissolvable rice glutelin was dispersed in 25 mL of an aqueous solution (5%, w/w), and 0.0125 g of another variety of rice glutelin was added. Then, 1 M of sodium hydroxide was added to adjust the solution to pH 12, so that the protein was fully dissolved in strong alkali. After stirring for 3 hours, 1 M of hydrochloric acid was added to acidify the solution to pH 10.5, and then 0.1 M of hydrochloric acid was used to adjust the solution to pH 7.5. The entire pH-cycle process needs to be carried out under a stirring condition. Finally, the salts and other small molecular compounds in the protein solution were removed by dialysis to obtain the film-forming solution of the experimental group. Then, 0.375 g of glycerol was added to the protein solution of the experimental group, and heated and stirred at 60° C. for 30 minutes, and degassed under vacuum for 10 minutes to remove air bubbles. Finally, 3 mL of the final film-forming solution was poured into a circular Teflon mold (3 cm in diameter) and dried in an oven at 40° C. The dried film was peeled off and placed in a constant temperature and humidity incubator at 25° C. and 40% relative humidity for 24 hours as a tribo-electron-donating layer for testing.

Preparation of triboelectric negative layer: The PTFE film was cut into a rectangle of 1.5 cm×1.5 cm as the tribo-electron-donating layer for testing.

Figure 3:
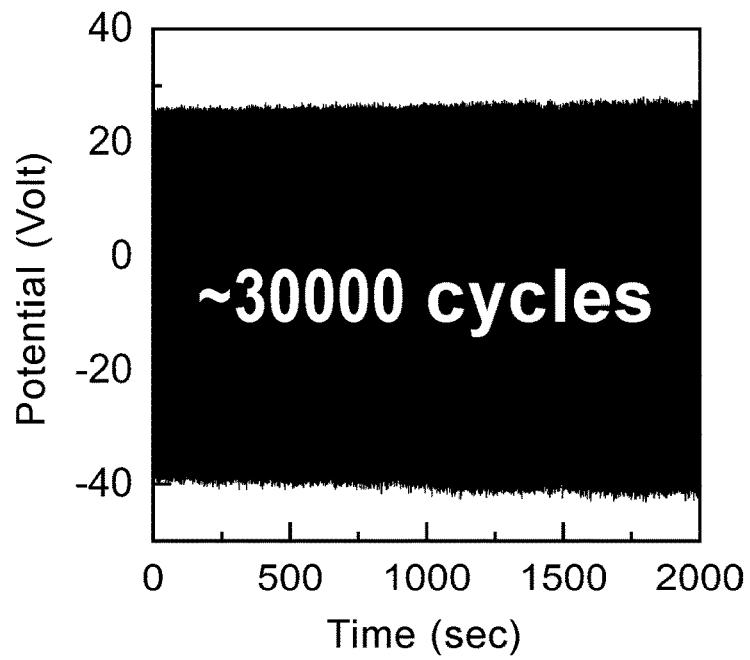
FIG. 3 is a fatigue test of a triboelectric nanogenerator based on the protein film of experimental group subjected to pH-cycle in the present disclosure, which shows good stability after 30,000 times of continuous operations.

Preparation of triboelectric nanogenerator: The above rice glutelin film and PTFE film were combined to form a triboelectric pair, and an aluminum foil was placed on one side of the protein film as an electrode to form a triboelectric nanogenerator, and the voltage signal thereof was measured with an oscilloscope. As shown in FIG. 3, after 30,000 times of cycles, the signal remained very stable.

Embodiment 4

First, a protein solution of the experimental group was prepared. 1.25 g of indissolvable rice glutelin was dispersed in 25 mL of an aqueous solution (5%, w/w), and 0.0125 g of another variety of rice glutelin was added. Then, 1 M of sodium hydroxide was added to adjust the solution to pH 12, so that the protein was fully dissolved in strong alkali. After stirring for 3 hours, 1 M of hydrochloric acid was added to acidify the solution to pH 10.5, and then 0.1 M of hydrochloric acid was used to adjust the solution to pH 7.5. The entire pH-cycle process needs to be carried out under a stirring condition. Finally, the salts and other small molecular compounds in the protein solution were removed by dialysis to obtain the film-forming solution of the experimental group.

Secondly, a protein solution of the control group was prepared. 1.25 g of indissolvable rice glutelin was dispersed in 25 mL of an aqueous solution (5%, w/w). Then, 1 M of sodium hydroxide was added to adjust the solution to pH 12, so that the protein was fully dissolved in strong alkali. After stirring for 3 hours, the film-forming solution of the control group was obtained.

Figure 4:
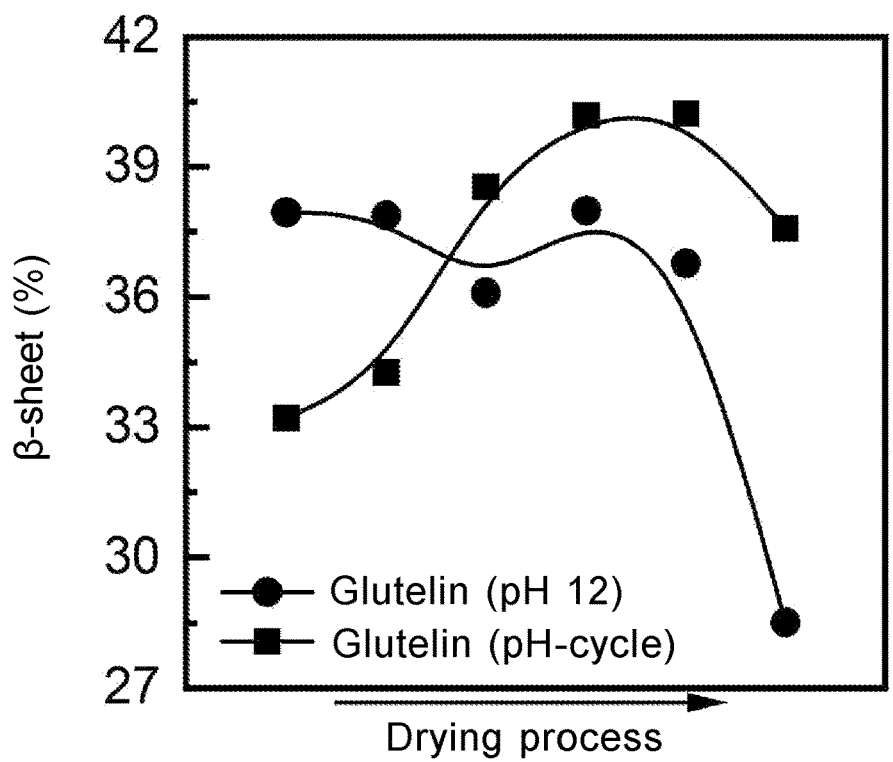
FIG. 4 shows the changes of the protein secondary structure during the forming process of the protein film in the experimental group (pH-cycle) and the control group (pH 12) estimated by the attenuated total reflection-Fourier-transform infrared spectrum (ATR-FTIR) in the present disclosure.

The protein solutions of the two groups were placed on a heating plate and heated at 40° C. In the early stage, the solutions were subjected to Fourier-transform infrared spectrum testing every one hour. In the later stage, due to the fast drying speed of the protein solutions, infrared testing was carried out every half an hour. The changes in protein secondary structure during the forming process of protein films of the experimental group and the control group were analyzed by infrared spectra, as shown in FIG. 4. The β-sheet content of the experimental group in the film-forming process did not change significantly, while the β-sheet content of the control group decreased significantly, indicating that the structure of the experimental group formed during the pH-cycle process was not destroyed. Moreover, high β-sheet content resulted in the exposure of a large number of amide groups. The strong alkalinity caused by the increase of sodium hydroxide content resulting from the evaporation of the solution during the film-forming process of the control group destroyed the structure of protein. As a result, exposure of amide groups exhibited randomness. Therefore, amide groups on the surface of the control group were significantly fewer than those of the experimental group, thus showing a weaker electron donating ability than the experimental group.

What is claimed is:

1. A method for improving a triboelectric output performance of a protein film by changing a protein structure, comprising pretreating a protein powder to obtain a protein solution, adding a plasticizer, and denaturing the protein through a heat treatment to obtain a more extensive structure required for film forming; evaporating a solvent and drying to obtain a transparent and flexible protein film with a uniform texture; wherein pretreating the protein powder to obtain the protein solution comprises co-dissolving a first protein powder and a minor amount of another protein powder in an alkaline aqueous solution and maintaining for a period of time, and performing an acidifying treatment to achieve neutral condition to form the protein solution under a neutral condition, wherein the first protein powder is a plant protein comprising rice protein, peanut protein isolate, soybean protein isolate, wheat glutelin, or zein, and wherein the alkaline aqueous solution is a sodium hydroxide solution to adjust pH to a range between 11 and 13, and is maintained for a period of time for 2 to 8 hours.

2. The method for improving the triboelectric output performance of the protein film by changing the protein structure according to claim 1, wherein the another protein powder is a protein powder with a protein structure different from the first protein powder, and a mass ratio between the first protein powder and the another protein powder is 1:0.005 to 1:0.1.

3. The method for improving the triboelectric output performance of the protein film by changing the protein structure according to claim 1, wherein the acidifying treatment adopts a step of adding hydrochloric acid and adjusting pH to a range between 6 and 8.

4. The method for improving the triboelectric output performance of the protein film by changing the protein structure according to claim 1, wherein the plasticizer is polyol, and an amount of addition of the plasticizer is 20 to 50% (w/w) of the protein powder.

5. The method for improving the triboelectric output performance of the protein film by changing the protein structure according to claim 1, wherein the process of obtaining the protein solution from the pretreatment is carried out under a stirring condition.

6. The method for improving the triboelectric output performance of the protein film by changing the protein structure according to claim 1, wherein the protein film serves as an electron-donating layer of a triboelectric nanogenerator, which is stacked face-to-face with a triboelectric negative layer, respective rear surfaces of the protein film and the triboelectric negative layer are adhered or plated with electrodes, or only the rear surface of the protein film or the rear surface of the triboelectric negative layer is provided with a grounded electrode, thereby fabricating the triboelectric nanogenerator.

7. The method for improving the triboelectric output performance of the protein film by changing the protein structure according to claim 6, wherein the triboelectric negative layer comprises polytetrafluoroethylene (Teflon), polydimethylsiloxane (PDMS), polyvinyl chloride (PVC), polyimide (Kapton), silicon rubber (Ecoflex), or polylactic acid (PLA).

8. The method for improving the triboelectric output performance of the protein film by changing the protein structure according to claim 6, wherein the triboelectric nanogenerator has four operating modes, comprising a vertical contact-separation mode, a lateral-sliding mode, a single-electrode mode and a freestanding triboelectric-layer mode.

* * * * *